United States Patent [19]

Aoyama et al.

[11] Patent Number: 4,916,058

[45] Date of Patent: Apr. 10, 1990

[54] METHOD AND TEST COMPOSITION FOR DETERMINATION OF HYDROGEN PEROXIDE

[75] Inventors: Norihito Aoyama; Akira Miike; Yoshiaki Shimizu, all of Shizuoka; Toshio Tatano, Numazu, all of Japan

[73] Assignee: Kyowa Medex Co., Ltd., Tokyo, Japan

[21] Appl. No.: 65,126

[22] Filed: Jun. 23, 1987

Related U.S. Application Data

[63] Continuation of Ser. No. 594,865, Mar. 29, 1984, abandoned.

[30] Foreign Application Priority Data

Mar. 31, 1983 [JP] Japan .................................. 58-56652

[51] Int. Cl.$^4$ .................... C12Q 1/62; C12Q 1/60; C12Q 1/54; C12Q 1/26; C12Q 1/28
[52] U.S. Cl. .................................. 435/10; 435/11; 435/14; 435/25; 435/28; 435/810; 436/66
[58] Field of Search ....................... 435/10–12, 435/14, 25, 28, 810; 436/66

[56] References Cited

U.S. PATENT DOCUMENTS

| | | | |
|---|---|---|---|
| 3,654,179 | 4/1972 | Bauer | 435/28 |
| 3,859,341 | 1/1975 | Jonsson et al. | 435/28 X |
| 4,384,042 | 5/1983 | Miike et al | 435/810 |
| 4,737,466 | 4/1988 | Klein et al. | 435/28 |
| 4,810,642 | 3/1989 | Aoyama et al. | 435/28 |
| 4,851,353 | 7/1989 | Miike et al. | 436/66 |

FOREIGN PATENT DOCUMENTS

| | | | |
|---|---|---|---|
| 0038205 | 10/1981 | European Pat. Off. | 435/28 |
| 0045220 | 2/1983 | European Pat. Off. | 435/28 |

*Primary Examiner*—Esther M. Kepplinger
*Attorney, Agent, or Firm*—Fitzpatrick, Cella, Harper & Scinto

[57] ABSTRACT

Disclosed is a method for the colorimetric determination of hydrogen peroxide in a sample by reacting a particular chromogen with the hydrogen peroxide in the presence of peroxidase and measuring the absorbancy of the reaction solution in the visible or near inflared ray region. Also disclosed is a test composition for carrying out the determination.

11 Claims, No Drawings

METHOD AND TEST COMPOSITION FOR DETERMINATION OF HYDROGEN PEROXIDE

This application is a continuation of application Ser. No. 594,865 filed Mar. 29, 1984 now abandoned.

BACKGROUND OF THE INVENTION

The present invention relates to a method and test composition for the determination of hydrogen peroxide, and more particularly, to a method for the determination of hydrogen peroxide by reacting hydrogen peroxide with a novel chromogen as a hydrogen donor in the presence of peroxidase and determining the degree of pigment formed. The invention also pertains to a test composition suitable for carrying out such determination.

Heretofore, the determination of a substrate is generally carried out by oxidizing the substrate by the action of oxidase and determining the formed hydrogen peroxide. For example, cholesterol is oxidized by cholesterol oxidase to form hydrogen peroxide. The hydrogen peroxide is then determined by reacting the hydrogen peroxide with a chromogen in the presence of peroxidase to form a pigment and measuring the absorbancy of the reaction solution colored by the formation of the pigment in the visible ray region. In such processes, 4-aminoantipyrine (hereinafter referred to as "4AA") and phenol, 4AA and N,N-dimethylaniline, 4AA and N-ethyl-N-(β-hydroxyethyl)-m-toluidine, 3-methylbenzothiazolin hydrazone and N,N-diethylaniline, 4AA and N-ethyl-N-(3-methylphenyl)-N'-acetylethylenediamine (hereinafter referred to as "EMAE") and the like are generally used as the chromogen.

While the known methods were acceptable, there is a need for chromogens which are superior in sensitivity and which are not affected by the components in vivo such as hemoglobin, bilirubin and uric acid.

SUMMARY OF THE INVENTION

It has now been found that a compound represented by either of the following formula (I) or (II) is excellent as a chromogen.

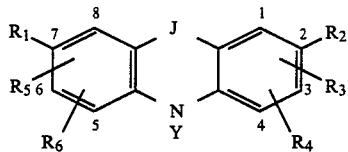

Formula (I)

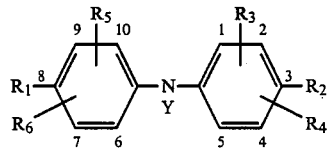

Formula (II)

In the above formulae, Y represents hydrogen or

Z represents an oxygen atom or a sulfur atom, X represents hydrogen, alkyl, alkenyl, aryl, aralkyl, amino or substituted amino, $R_1$ represents hydroxyl, amino or substituted amino, $R_2$ represents hydrogen, hydroxyl, alkyl, alkoxy, aryl, aralkyl, alkenyl, amino or substituted amino, $R_3$ represents groups represented by the general formula (III), (IV), (V), (VI) or (VII) described hereinafter, $R_4$ $R_5$ or $R_6$ may be the same or different and represents hydrogen, alkyl, alkenyl, acyl, aryl, aralkyl, halogen atom, nitro, sulfo, carboxyl, hydroxyl, alkoxy or groups represented by the general formula (III), (IV), (V), (VI) or (VII), J represents —S—, —O—, the general formula

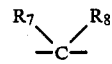

or the general formula

$R_7$ and $R_8$ are the same or different and represent hydrogen, alkyl or alkenyl, and $R_5$ and $R_6$ may form alkenylene.

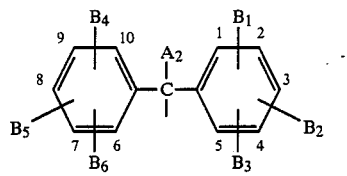

General formula (III)

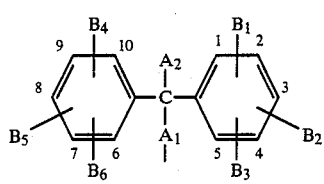

General formula (IV)

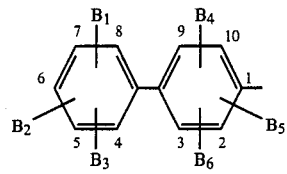

General formula (V)

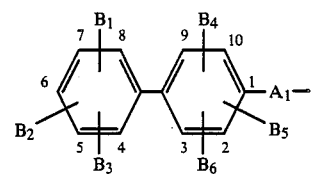

General formula (VI)

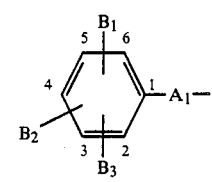

General formula (VII)

In the formulae, $A_1$ represents alkylene, $A_2$ has the same meaning as $R_2$, $B_1$, $B_2$, $B_3$, $B_4$, $B_5$ or $B_6$ may be the same or different and represents hydrogen, alkyl, alkenyl, acyl, aryl, aralkyl, halogen, atom, nitro, sulfo, carboxyl, hydroxyl, alkoxy or hydroxyalkyl.

As the substituent of substituted amino in the definition of $R_1$ and $R_2$, alkyl, alkenyl, aryl, hydroxyalkyl, cycloalkyl, acyl, aralkyl, acylalkyl, carboxyl, alkoxy, sulfo, sulfoalkyl, etc are mentioned.

As used herein, alkyl includes alkyl having 1 to 5 carbon atoms, such as methyl, ethyl, propyl and butyl; alkenyl includes alkenyl having 2 to 5 carbon atoms such as vinyl, propylene and butylene; alkoxy includes alkoxy having 1 to 5 carbon atoms such as methoxy, ethoxy, propoxy and butoxy; aryl includes phenyl, naphtyl, and substituted phenyl; substituent of substituted phenyl includes alkyl having 1 to 4 carbon atoms, halogen such as chloro atom and bromo atom, amino, alkoxycarbonylamino, alkoxycarbonylaminoalkyl, alkoxy and acyl; substituted phenyl may have 1 to 5 substituents; aralkyl includes aralkyl having 7 to 10 carbon atoms such as benzyl; acyl includes acyl having 2 to 5 carbon atoms such as acetyl, propionyl and butyryl; halogen includes fluoro atom, chloro atom and bromo atom.

Alkenylene includes alkenylene having 3-4 carbon atoms such as —CH=CH—CH=CH—, —CH=CH—CH$_2$—, etc.

In accordance with the present invention, hydrogen peroxide in a sample can be determined by reacting the hydrogen peroxide with Compound (I) or (II) and measuring the absorbancy of the reaction solution colored by the formation of a pigment at a maximum absorption wave length of the pigment, in a visible or near infrared ray region.

The principle of the present invention is on the basis of the fact that the reaction of hydrogen peroxide with the present chromogen proceeds stoichiometrically to form a pigment and the amount of formed pigment is proportional to the amount of hydrogen peroxide in the sample.

In carrying out the present invention, the compound (I) or (II) and peroxidase are added to a sample containing hydrogen peroxide or to the system where hydrogen peroxide is produced (hereinafter referred to as "H$_2$O$_2$-producing system"). The absorbancy of the reaction solution colored by the formation of a pigment is measured in the visible or near infrared ray region, 600-900 nm. On the other hand, the standard curve showing the relation between the amount of hydrogen peroxide and absorbancy is separately prepared by using a standard hydrogen peroxide solution as the sample. The amount of hydrogen peroxide in the sample is calculated by applying the obtained absorbancy to the standard curve.

The reaction is usually carried out at a temperature of 5°-50° C., preferably 25°-40° C. in a buffer solution having a pH of 2-10 and is completed in several minutes.

The chromogen is used in an equimolar amount with hydrogen peroxide or more, preferably 10-1000 mole equivalents. Peroxidase is used in a concentration of 0.1-1000 IU/ml.

As buffers, Good's buffer [a generic term for buffers containing compounds such as, for example, N-(2-acetamido)-2-aminoethanesulfonic acid and the like sold by Sigma Corporation], phosphate buffer, tris-HCl buffer, succinate buffer, citrate buffer, acetate buffer, etc. may be used in a concentration of 0.005-2 mol/l.

Small amount of phenol or EMAE can be added to the reaction system for activating peroxidase or for promoting the reaction of pigment formation.

Examples of the chromogen used in the present invention are shown in Tables 1 and 2, wherein the symbols in tables have the following means.
P: Structure of the compound
M:.CH$_3$
E: C$_2$H$_5$
D: CH$_2$CH$_2$CH$_2$SO$_3$H
α$_1$: CH$_2$CH$_2$CH$_3$
α$_2$: >CHCH$_2$CH$_2$CH$_3$

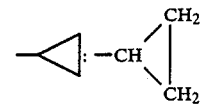

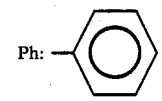

R$_4$, R$_6$, B$_2$, B$_3$, B$_5$ and B$_6$ in the compounds represent hydrogen. Y means H in Table 1 and means $$-\overset{O}{\underset{\|}{C}}-Ph$$

in Table 2. "J" means "—S—" in Compounds Nos. 18 and 19.

TABLE 1

| Compound No. | P | R$_1$ | R$_2$ | R$_3$ | R$_5$ | A$_1$ | A$_2$ | B$_1$ | B$_4$ |
|---|---|---|---|---|---|---|---|---|---|
| 1 | II | NM$_2$ | NM$_2$ | III | III | — | H | Cl | H |
| 2 | " | " | " | " | " | — | " | F | H |
| 3 | " | " | " | " | " | — | " | H | H |
| 4 | " | " | " | " | " | — | " | OM | OM |
| 5 | " | " | " | " | " | — | " | Cl | Cl |
| 6 | " | " | " | " | " | — | " | F | F |
| 7 | " | " | " | " | " | — | " | NM$_2$ | NM$_2$ |
| 8 | " | " | " | " | H | — | " | Cl | Cl |
| 9 | " | " | " | " | III | — | " | H | H |
| 10 | " | " | " | IV | H | CH$_2$ | H | Cl | Cl |
| 11 | " | " | " | " | " | " | M | " | " |
| 12 | " | " | " | V | V | " | — | H | H |
| 13 | " | " | " | III | H | — |  | " | " |
| 14 | " | " | " | " | " | — | α$_1$ | " | " |
| 15 | " | " | " | VII | " | α$_2$ | — | " | " |
| 16 | " | " | " | " | VII | CH$_2$ | — | Cl | — |

TABLE 1-continued

| Compound No. | P | $R_1$ | $R_2$ | $R_3$ | $R_5$ | $A_1$ | $A_2$ | $B_1$ | $B_4$ |
|---|---|---|---|---|---|---|---|---|---|
| 17 | " | " | " | " | " | $CH_2$ | — | B$\gamma$ | — |
| 18 | I | $NM_2$ | $NM_2$ | III | III | $CH_2$ | H | Cl | Cl |
| 19 | " | " | " | " | $NH_2$ | — | " | Cl | Cl |
| 20 | II | $NH_2$ | OH | " | H | — | " | Cl | Cl |
| 21 | " | " | OM | " | " | — | " | Cl | Cl |
| 22 | " | " | " | " | " | — | " | F | F |
| 23 | " | " | OH | " | " | — | " | F | F |
| 24 | " | " | " | " | III | — | " | Cl | Cl |
| 25 | " | " | " | " | " | — | " | F | F |
| 26 | " | " | " | " | " | — | " | H | H |
| 27 | " | " | " | " | " | — | " | H | F |
| 31 | II | — | $ND_2$ | $ND_2$ | " | III | " | H | H |
| 32 | II | — | " | " | " | " | " | Cl | Cl |
| 33 | II | — | NHD | NHD | " | " | " | H | H |
| 34 | II | — | " | " | " | " | " | Cl | Cl |

TABLE 2

| Compound No. | P | J | $R_1$ | $R_2$ | $R_3$ | $R_5$ | $A_2$ | $B_1$ | $B_4$ |
|---|---|---|---|---|---|---|---|---|---|
| 28 | II | — | $NM_2$ | $NM_2$ | III | III | H | Cl | Cl |
| 29 | I | S | " | " | " | H | " | " | " |
| 30 | I | O | $NE_2$ | $NE_2$ | " | " | " | " | " |
| 31 | II | — | $ND_2$ | $ND_2$ | " | III | " | H | H |
| 32 | II | — | " | " | " | " | " | Cl | Cl |
| 33 | II | — | NHD | NHD | " | " | " | H | H |
| 34 | II | — | " | " | " | " | " | Cl | Cl |

Comparative tests between the compounds indicated in Tables 1 and 2 and known compounds in respect of the degree of color development, etc. are conducted according to the following method.

Good buffer solution (pH 6.5) containing 10 U/ml peroxidase, 0.001 mg/ml phenol, 0.1 mg/ml Triton X-100, 0.1 mg/ml compound (I) or (II) is prepared. To 20 μl of 10.33 mg/dl $H_2O_2$ solution is added 3 ml of the solution and the mixture is subjected to reaction.

The OD value of the reaction solution at λmax is measured.

The results are shown in Table 3 defining the OD value obtained by using 4AA-EMAE as 100.

The effect of components in serum such as bilirubine, cysteine and uric acid is measured by existing 20 μg/3 ml bilirubin, 20 μg/3 ml of cysteine or 10 μg/3 ml of uric acid in a sample. The symbol "±" means that the effect is 3-6%, "+" means that the effect is "6-20"%, "++" means that the effect is more than 20% and "—" means that the effect is less than 3%.

The degree of the color development in reagent blank is shown as compared with that of the color development obtained by using the representative Leuco Bindschedler's, Leuco Bindschedler's Green (LBG) as chromogen.

"AA" means that the degree of color development is very low. "A" means that that is low and "B" means that that is equal to that of LBG.

As the sensitivity is higher and the degree of color development in reagent blank is lower, the chromogen as hydrogen donor is better and the trace amount of the component can be determined by using the chromogen.

TABLE 3

| Compound No. | λ max (nm) | S | F B | F CY | F U | RB |
|---|---|---|---|---|---|---|
| 1 | 747 | 390 | ± | ± | ± | A |
| 2 | 740 | 395 | ± | ± | ± | A |
| 3 | 735 | 380 | — | — | — | AA |
| 4 | 700 | 150 | + | + | ± | AA |
| 5 | 755 | 400 | — | — | — | AA |
| 6 | 745 | 400 | — | — | — | AA |
| 7 | 520 | 360 | ± | ± | ± | AA |
| 8 | 750 | 350 | " | " | ± | A |
| 9 | 720 | 200 | " | + | + | A |
| 10 | 728 | 400 | " | + | + | A |
| 11 | 690 | 200 | " | + | + | A |
| 12 | 733 | 410 | " | + | ± | AA |
| 13 | 728 | 370 | " | + | " | A |
| 14 | 725 | 360 | " | + | " | A |
| 15 | 747 | 390 | " | ± | " | B |
| 16 | 737 | 380 | " | + | " | A |
| 17 | 735 | 370 | ± | ± | ± | A |
| 18 | 680 | 700 | " | " | " | B |
| 19 | 670 | 400 | " | " | " | B |
| 20 | 700 | 200 | " | " | " | A |
| 21 | 690 | 160 | " | " | " | A |
| 22 | 723 | 310 | " | " | " | A |
| 23 | 715 | 150 | " | " | " | A |
| 24 | 708 | 270 | — | — | — | AA |
| 25 | 700 | 270 | — | — | — | AA |
| 26 | 710 | 250 | — | ± | — | AA |
| 27 | 715 | 260 | — | ± | — | AA |
| 28 | 755 | 395 | ± | ± | ± | AA |
| 29 | 680 | 700 | ± | ± | ± | B |
| 30 | 685 | 690 | ± | ± | ± | B |
| 31 | 760 | 350 | — | — | — | AA |
| 32 | 770 | 350 | — | — | — | AA |
| 33 | 710 | 320 | — | — | — | A |
| 34 | 720 | 320 | — | — | — | A |
| $RE_1$ | 728 | 410 | + | + | + | B |
| $RE_2$ | 555 | 100 | ++ | ++ | ++ | A |

$RE_1$:LBG
$RE_2$:4AA-EMAE
S:Sensitivity
F:Effect of some components in serum
B:Bilirubin
CY:Cysteine
U:Uric acid
RB:Degree of color development of reagent blank The chromogens used in the present invention are obtained by condensation reaction of Leuco bases obtained by reduction reaction of diphenyl amines, thiazine pigments or oxazine pigments with benzhydrols in the presence of sulfuric acid. The condensation reaction is carried out at 30°-100° C. for 1-100 hours. The reaction mixture is added to an organic solvent capable of crystallizing the desired chromogen such as n-octanol. The crude crystals are dissolved in an organic solvent such as methanol and the solution is subjected to column chromatography using silica gel to remove the desired compound.

The method for production of compounds indicated in Tables 1 and 2 is illustrated below.

(1) Production of Compound Nos. 1-7, 12, 16 and 17

Bindschedler's Green Leuco base [4,4'-bis(dimethylamino)diphenylamine] (hereinafter referred to as "BGLB") and each of the undermentioned compounds in a molar ratio of 1:2 are added to 60% sulfuric acid in an amount of 5 times on the basis of Leuco base. The mixture is subjected to reaction at 80° C. for 2-3 hours while stirring.

The reaction mixture is added to n-octanol to crystallize the desired product and the crude crystals are dissolved in a small amount of methanol. The methanol is subjected to column chromatography using silica gel. The elution is carried out with chloroform/n-hexane=2/1. The fractions containing the desired compound are collected and concentrated to dryness to obtain the desired compound.

| Compound No. | Melting Point (°C.) | Reactant |
| --- | --- | --- |
| 1 | 102-105 | 4-chlorobenzhydrol |
| 2 | 98-101 | 4-Fluorobenzhydrol |
| 3 | 120-123 | Benzhydrol |
| 4 | 152-155 | 4,4'-Dimetoxybenzhydrol |
| 5 | 184-187 | 4,4'-Dichlorobenzhydrol |
| 6 | 111-114 | 4,4'-Difluorobenzhydrol |
| 7 | 89-92 | 4,4'-Dimethylaminobenzhydrol |
| 12 | 108-111 | 4-Biphenylmethanol |
| 16 | 95-98 | P-chlorobenzylalcohol |
| 17 | 104-107 | P-bromobenzylalcohol |

(2) Production of Compound Nos. 8, 10, 11 and 13-15

The same procedures as described in (1) above are repeated except that the reaction of BGLB with the following compounds in a molar ratio of 10:1 is carried out at 50° C.

| Compound No. | M. P. (°C.) | Reactant |
| --- | --- | --- |
| 8 | 78-81 | 4,4'-Dichlorobenzhydrol |
| 10 | 131-133 | 2,2'-Bis(p-chlorophenyl)-ethanol |
| 11 | 128-131 | 2,2'-Bis(p-chlorophenyl)-propanol |
| 13 | 82-85 | Cyclopropyl-benzhydrol |
| 14 | 84-87 | 1,1'-Diphenylbutanol |
| 15 | 172-175 | 1-Phenylbutanol |

(3) Production of Compound Nos. 9 and 24-27

The same procedures as described in (1) above are repeated except that the reaction of sulfate of 4,4'-diamino-diphenyl amine with diphenylmethanol, 4,4'-dichlorobenzhydrol, 4,4'-difluorobenzhydrol, 4-chlorobenzhydrol, or 4-fluorobenzhydrol is carried out to obtain the desired compounds having M.P. of 158°-161° C., 173°-175° C., 89°-92° C., 155°-158° C. and 104°-106° C., respectively.

(4) Production of Compound Nos. 18 and 19

The same procedures as described in (1) above are repeated except that the reaction of compounds obtained by reduction reaction of Methylene Blue (C.I. 52015) or Methylene Green (C.I. 52020) with 4,4'-dichlorobenzhydrol in a molar ratio of 10:1 is carried out at 50° C. to obtain the desired compounds having M.P. of 179°-180° C. and 148°-151° C., respectively.

(5) Production of Compound No. 29

The same procedures as described in (1) above are repeated except that the reaction of benzoyl Leuco Methylene Blue with 4,4'-dichlorobenzhydrol in a molar ratio of 10:1 is carried out at 50° C. to obtain Compound No. 29 (M.P. 212°-215° C.)

(6) Production of Compound No. 28

The same procedures as described in (1) above are repeated except that the reaction of Compound No. 5 with phenyl iso-cyanate is carried out in dimethylformamide (DMF) at 50° C. for 3 days to obtain Compound No. 28 (M.P. 196°-200° C.).

(7) Production of Compound No. 30

Compound obtained by reduction of Basic Blue (C.I. 51004) using sodium borohydride and 4,4'-dichlorobenzhydrol in a molar ratio of 10:1 are added to 60% sulfuric acid. The mixture is subjected to reaction at 50° C. and the same purification procedures as described in (1) above are repeated.

The obtained compound and iso-cyanic acid in an equal molar amount are added to DMF and the mixture is subjected to reaction at 50° C. for 3 days. The same purification procedures as described in (1) above are repeated to obtain Compound No. 30 (M.P. 118°-120° C.).

(8) Production of Compound Nos. 20 and 23

The same procedures as described in (1) above are repeated except that the reaction of P-(p-aminoanilino)-phenol with 4,4'-dichlorobenzhydrol (No. 20) or 4,4'-difluorobenzhydrol (No. 23) in a molar ratio of 10:1 is carried out in 60% sulfuric acid at 50° C. to obtain Compound No. 20 (M.P. 89°-91° C.) or Compound No. 23 (M.P. 121°-123° C.), respectively.

(9) Production of Compound Nos. 21 and 22

The same procedures as described in (1) above are repeated except that the reaction of Variamine Blue hydrochloride with 4,4'-dichlorobenzhydrol (No. 21) or 4,4'-difluorobenzhydrol (No. 22) in a molar ratio of 10:1 is carried out in 60% sulfuric acid at 50° C. to obtain Compound No. 21 (M.P. 163°-165° C.) and Compound No. 22 (M.P. 158°-160° C.), respectively.

(10) Production of Compound Nos. 31-34

4,4'-diamino-diphenylamine sulfate and propane sultone in a molar ratio of 1:20 are added to chloroform and the mixture is subjected to reaction at 50° C. for 5-7 days with stirring. Distilled water in a same amount of the reaction mixture is added to the reaction mixture. After vigorously stirring, the water layer is separated and concentrated to dryness. The dried material and benzhydrol (No. 31, 33) or 4,4'-dichlorobenzhydrol (No. 32, 34) in a weight ratio of 2:1 are added to 60% sulfuric acid. The mixture is subjected to reaction at 80° C. for 2-3 hours with stirring.

The same purification procedures as described in (1) above are repeated except that solvent, the polarity of which is different is used. The elution is started from chloroform. Compound No. 33 or 34 are obtained when the solvent having the lower polarity is used. Then, Compound No. 31 or 32 is obtained.

| M. P. Compound No. 31 | 93-95° C. |
| --- | --- |
| M.P. Compound No. 32 | 78-82° C. |
| M.P. Compound No. 33 | 62-65° C. |
| M.P. Compound No. 34 | 45-48° C. |

The present method may apply for the determination of reactants or enzymatic activity in the $H_2O_2$-producing system.

Particularly, when the system is an enzymatic reaction, both the $H_2O_2$-producing system and the system where pigment is produced [hereinafter referred to as pigment-producing system] proceed at the same time in the same system and therefore, such a method is simple and convenient.

Such enzymatic reaction includes the combination of oxidase and a substrate thereof, examples of which are the combination are uric acid-uricase, cholesterol-cholesterol oxidase, cholesterol ester-cholesterol esterase and cholesterol oxidase, xanthine, hypoxanthine or guanine-xanthine oxidase, phospholipase D-lectin-choline oxidase, choline-choline oxidase, pyruvic acid-pyruvate oxidase-phosphoric acid, triglyceride-lipoprotein lipase-ATP-glycerinkinase-glycerin-3-phosphate oxidase, fatty acid-coenzyme A-acyl Co A synthetase-acyl Co A oxidase, triglyceride-lipase-glycerol oxidase, glucose-glucose oxidase and galactose-galactose oxidase.

The substrates of these enzymatic reactions are contained in serum, urea, etc. and the determination of the substrates is useful for diagnostic purposes.

Examples of enzymatic reaction are schematically shown as follows:

1. Uric acid

Uric acid + $O_2$ + $2H_2O$ $\xrightarrow{\text{Uricase}}$ Allantoin + $CO_2$ + $H_2O_2$ 2. Total cholesterol cholesterol ester + $H_2O$ $\xrightarrow{\text{cholesterol esterase}}$ Free form of cholesterol + Fatty acid Free form of cholesterol +

$O_2$ $\xrightarrow{\text{cholesterol oxidase}}$ cholesterone + $H_2O_2$

3. Triglyceride

Triglyceride + $3H_2O$ $\xrightarrow{\text{lipoprotein lipase}}$ Glycerol + Fatty acid Glycerol + $O_2$ $\xrightarrow{\text{Glycerol oxidase}}$ Glyceraldehyde + $H_2O_2$ 4. Free form of fatty acid
Free form of fatty acid + ATP +

CoA $\xrightarrow{\text{Acyl-CoA synthetase}}$ Acyl-CoA + AMP + PPi

Acyl-CoA + $O_2$ $\xrightarrow{\text{Acyl-CoA oxidase}}$

Trans-2,3-dehydroacyl-CoA + $H_2O_2$

5. Sialic acid

Sialic acid (bound type) $\xrightarrow{\text{Neuraminidase}}$

N-Acetyl neuraminic acid (NANA)

NANA $\xrightarrow[\text{+ Pyruvic acid}]{\text{NANA-aldolase}}$ N-acetylmannosamine + Pyruvic acid Pyruvic acid + $O_2$ +

Phosphoric acid $\xrightarrow[\text{Thimaine pyrolic acid, Mg}]{\text{Pyruvate oxidase}}$ $H_2O_2$ + Acetylphosphoric acid + $CO_2$ 6. Pyruvic acid
Pyruvic acid + $O_2$ +

Phosphoric acid $\xrightarrow[\text{Thimaine pyrolic acid, Mg}]{\text{Pyruvate oxidase}}$ $H_2O_2$ + Acetylphosphoric acid + $CO_2$ 7. Glucose Glucose + $O_2$ $\xrightarrow{\text{Pyranose oxidase}}$ D-glucosone + $H_2O_2$ 8. Inorganic phosphorus $HPO_4^{--}$ + Inosine $\xrightarrow{\text{Purine nucleotide phosphorylase}}$ Hypoxanthine + Ribose-1-phosphoric acid Hypoxanthine + $2H_2O$ + $O_2$ $\xrightarrow{\text{Xanthine oxidase}}$ Uric acid + $2H_2O_2$ 9. Phospholipid Lecitin $\xrightarrow{\text{Phospholipase D}}$ Choline + Phosphatidyl acid Choline $\xrightarrow{\text{Choline oxidase}}$ $2H_2O_2$ + Betaine 10. Monoamine oxidase Monoamines + $O_2$ + $H_2O$ $\xrightarrow{\text{Monoamine oxidase}}$ Acrolein + $NH_3$ + $H_2O_2$ 11. Choline esterase o-Toruoylcholine + $H_2O$ $\xrightarrow{\text{Choline esterase}}$ o-Toruyl acid + Choline Choline + $2O_2$ + $H_2O$ $\xrightarrow{\text{Choline oxidase}}$ Betaine + $2H_2O_2$ The hydrogen peroxide-producing reaction and pigment-producing reaction may be conducted stepwise or preferably, the determination of hydrogen peroxide is performed by adding to the sample the components necessary for the determination of hydrogen peroxide conducting all the reactions in one step and measuring the absorbancy of the reaction solution.

The components comprises oxidase for the substrate to be determined, peroxidase; compound (I) or (II). A buffer solution and surfactant, etc. may be added, if necessary. Of course, if components for oxidizing the substrate in addition to oxidase for the substrate are required, such components must be added to the $H_2O_2$-producing system.

Another aspect of the present invention is to provide a test composition for the determination of hydrogen peroxide which comprises oxidase for the substrate to be determined, the chromogen represented by the formula (I) or (II) and peroxidase. The composition may also contain a buffer reagent as well as surfactants such as polyoxyethylenealkylether, antiseptics such as sodium azide, ascorbate osidase for decomposing ascorbic acid, etc. if necessary. Further the composition may contain components necessary for producing hydrogen peroxide other than oxidase for the substrate.

Certain specific embodiments of the invention are illustrated by the following representative examples.

EXAMPLE 1

In this example 18 U of uricase, 100 U of peroxidase, 100 mg of Triton X-100, 0.1 mg of phenol and (A) 100 mg of 4AA and 100 mg of EMAE, (B) 50 mg of LBG, (C) 22.5 mg of Compound No. 3, (D) 22.5 mg of Compound No. 5, (E) 22.5 mg of Compound No. 6, (F) 22.5 mg of Compound No. 32 or (G) 22.5 mg of Compound No. 33 are dissolved in 100 ml of 50 mM Good buffer solution (pH 6.5) to prepare a reagent solution. To a test tube are poured 20 μl of serum and 3 ml of the reagent solution and the mixture is incubated for reaction at 37° C. for 10 minutes.

The absorbancy of each reaction solution at λmax is measured using reaction blank as a control. The concentration of uric acid in the serum is calculated by using calibration curve prepared in advance.

For comparison, the same test sample is analyzed by ultra violet spectrophotometric method of uricarse. The results are shown in Table 4.

TABLE 4

| Serum No. | Uric acid content (mg/dl) | | | | | | | |
|---|---|---|---|---|---|---|---|---|
| | Control | A | B | C | D | E | F | G |
| 1 | 5.7 | 5.9 | 5.0 | 5.7 | 5.6 | 5.7 | 5.7 | 5.6 |
| 2 | 2.8 | 3.8 | 4.0 | 2.9 | 2.7 | 2.7 | 2.7 | 2.8 |
| 3 | 11.0 | 9.2 | 12.8 | 11.0 | 11.0 | 11.0 | 11.1 | 11.1 |
| 4 | 4.0 | 5.8 | 4.9 | 4.1 | 4.1 | 3.9 | 4.0 | 3.9 |
| 5 | 6.2 | 6.5 | 6.5 | 6.1 | 6.1 | 6.3 | 6.1 | 6.0 |

EXAMPLE 2

In this example, 15 U of cholesterol oxidase, 20 U of cholesterol esterase, 150 U of peroxidase, 100 mg of Triton X-100, 0.1 mg of phenol and the chromogens (A-G) in Example 1 are dissolved in 50 mM of Good buffer solution (pH 5.8) to prepare a reagent solution. Ten μl of serum and 3 ml of the reagent solution are poured into a test tube and the mixture is incubated for reaction at 37° C. for 10 minutes. The absorbancy of the reaction solution at λmax is measured using reagent blank as a control. The concentration of cholesterol in serum is culculated by using the calibration curve prepared in advance.

For comparison, the same sample is subjected to analysis according to chromatography method (GC).

The results are shown in Table 5.

TABLE 5

| Serum No. | Cholesterol content (mg/dl) | | | | | | | |
|---|---|---|---|---|---|---|---|---|
| | GC | A | B | C | D | E | F | G |
| 1 | 92 | 82 | 102 | 90 | 91 | 89 | 89 | 93 |
| 2 | 243 | 248 | 280 | 240 | 242 | 242 | 241 | 242 |
| 3 | 100 | 90 | 115 | 99 | 100 | 98 | 100 | 100 |
| 4 | 178 | 169 | 193 | 178 | 176 | 179 | 177 | 178 |
| 5 | 112 | 120 | 140 | 111 | 111 | 112 | 111 | 112 |

EXAMPLE 3

In this example 9 U of acyl CoA synthetase, 57 U of acyl-CoA oxidase, 833 U of peroxidase, 200 mg of ATP, 27 mg of CoA, 70 mg of MgCl$_2$.6H$_2$O, 100 mg of Triton X-100, 0.1 mg of phenol and the chromogens (A-G) used in Example 1 are dissolved in 100 ml of 0.1M Good buffer solution (pH 6.75) to prepare a reagent solution. To 20 μl of serum sample is added 3 ml of the reagent solution and the mixture is subjected to reaction at 37° C. for 10 minutes. The absorbancy of the reaction solution at λmax is measured using reagent blank as a control and the concentration of free fatty acid in serum is calculated from the calibration curve. For comparison, the same samples are determined according to gas chromatograph method (GC) and the results are shown in Table 6.

TABLE 6

| Serum No. | Free fatty acid content (mg/dl) | | | | | | | |
|---|---|---|---|---|---|---|---|---|
| | GC | A | B | C | D | E | F | G |
| 1 | 80 | 53 | 102 | 82 | 80 | 79 | 79 | 81 |
| 2 | 115 | 180 | 160 | 115 | 118 | 116 | 114 | 115 |
| 3 | 102 | 42 | 280 | 101 | 100 | 101 | 102 | 101 |
| 4 | 258 | 290 | 295 | 260 | 261 | 259 | 259 | 257 |
| 5 | 180 | 300 | 220 | 180 | 179 | 179 | 181 | 179 |

EXAMPLE 4

In this example, 100 ml of Good buffer solution (pH 6.0) containing 140 mg of potassium dihydrogen phosphate, 23 mg of thiamine pyrophosphoric acid, 27 mg of MgCl$_2$.6H$_2$O, 300 U of pyruvate oxidase, 100 U of peroxidase, 100 mg of Triton X-100, 0.1 mg of phenol and (A) 100 mg of 4AA and 100 mg of EMAE, (B) 50 mg of LBG, (C) 22.5 mg of Compound No. 5, (D) 22.5 mg of Compound No. 24, (E) 22.5 mg of Compound No. 25, (F) 22.5 mg of Compound No. 26 or (G) 22.5 mg of Compound No. 27 is prepared as a reagent solution. To 50 μl of serum sample is added 3 ml of the reagent solution and the mixture is subjected to reaction at 37° C. for 10 minutes. The absorbancy of the reaction solution at λmax is measured using reagent blank as a control.

The concentration of pyruvate in the sample is calculated from the calibration curve and the results are shown in Table 7. For comparison, the same sample is determined according to UV method using lactate dehydrogenase.

TABLE 7

| Sample No. | Pyruvic acid content (mg/dl) | | | | | | | |
|---|---|---|---|---|---|---|---|---|
| | UV | A | B | C | D | E | F | G |
| 1 | 0.38 | 0.53 | 0.69 | 0.38 | 0.38 | 0.36 | 0.37 | 0.38 |
| 2 | 0.91 | 1.81 | 0.76 | 0.93 | 0.90 | 0.91 | 0.91 | 0.89 |
| 3 | 0.55 | 0.22 | 1.10 | 0.57 | 0.53 | 0.57 | 0.55 | 0.53 |
| 4 | 0.72 | 1.01 | 1.31 | 0.70 | 0.71 | 0.70 | 0.74 | 0.70 |
| 5 | 0.50 | 0.63 | 0.33 | 0.49 | 0.49 | 0.50 | 0.48 | 0.52 |

What is claimed is:

1. A method for the determination of hydrogen peroxide in a sample which comprises reacting the hydrogen peroxide with a chromogen represented by the formula

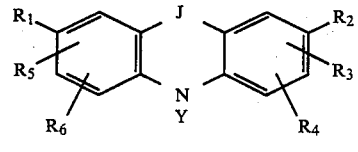

or

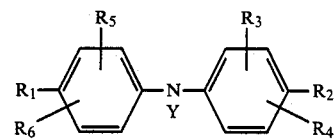

wherein Y represents hydrogen or

Z represents an oxygen atom or a sulfur atom, X represent hydrogen, alkyl, alkenyl, aryl, aralkyl, amino or substituted amino, $R_1$ represents hydroxyl, amino or substituted amino, $R_2$ represents hydrogen, hydroxyl, alkyl, alkoxy, aryl, aralkyl, alkenyl, amino or substituted amino, $R_3$ represents groups represented by the general formula (III), (IV), (V) or (VI) described hereinafter, $R_4$, $R_5$ or $R_6$ may be the same or different and represents hydrogen, alkyl, alkenyl, acyl, aryl, aralkyl, halogen atom, nitro, sulfo, carboxyl, hydroxyl, alkoxy or groups represented by the general formula (III), (IV), (V), (VI) or (VII) described hereinafter, J represents —S—, —O—, the general formula

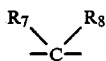

or the general formula

$R_7$ and $R_8$ are the same or different and represent hydrogen atom, alkyl or alkenyl, and $R_5$ and $R_6$ may form alkenylene:

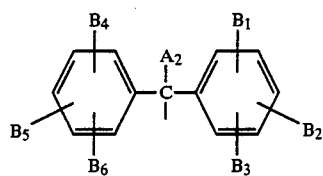    general formula (III)

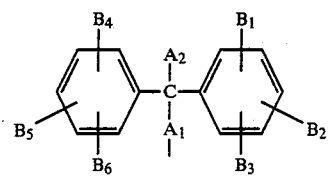    general formula (IV)

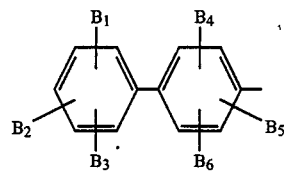    general formula (V)

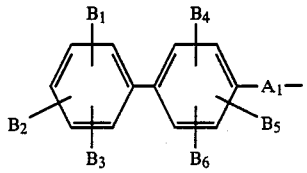    general formula (VI)

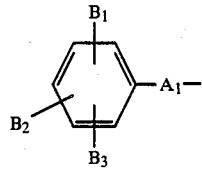    general formula (VII)

wherein $A_1$ represents alkylene, $A_2$ has the same meaning as that of $R_2$, $B_1$, $B_2$, $B_3$, $B_4$, $B_5$ or $B_6$ may be the same or different and represents hydrogen atom, alkyl, alkenyl, acyl, aryl, aralkyl, halogen atom, nitro, sulfo, carboxyl, hydroxyl, alkoxy or hydroxyalkyl; in the presence of peroxidase and measuring the absorbancy of the reaction solution in the visible or near infrared ray region.

2. A method according to claim 1, wherein said hydrogen peroxide is a product formed by enzymatic reaction.

3. A method according to claim 2, wherein said enzymatic reaction is the oxidation of a substrate using oxidase.

4. A method according to claim 3, wherein said oxidase is selected from the group consisting of uricase, cholesterol oxidase, xanthine oxidase, choline oxidase, pyruvate oxidase, glycerine-3-phosphate oxidase, acyl Co A oxidase, glycerol oxidase, glucose oxidase and galactose oxidase.

5. A method according to claim 2, wherein said hydrogen peroxide-producing reaction and the reaction of hydrogen peroxide with said chromogen are conducted simultaneously.

6. A method according to claim 1, wherein said reaction is carried out in a buffer solution.

7. A test composition for the determination of hydrogen peroxide, comprising peroxidase and chromogen represented by the formula

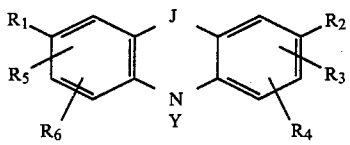

or

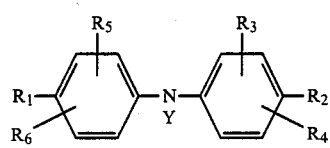

wherein Y represents hydrogen or

Z represents an oxygen atom or a sulfur atom, X represents hydrogen, alkyl, alkenyl, aryl, aralkyl, amino or substituted amino, $R_1$ represents hydroxyl, amino or substituted amino, $R_2$ represents hydrogen, hydroxyl, alkyl, alkoxy, aryl, aralkyl, alkenyl, amino or substituted amino, $R_3$ represents groups represented by the general formula (III), (IV), (V) or (VI) described hereinafter, $R_4$, $R_5$ or $R_6$ may be the same or different and represents hydrogen, alkyl, alkenyl, acyl, aryl, aralkyl, halogen atom, nitro, sulfo, carboxyl, hydroxyl, alkoxy or groups represented by the general formula (III), (IV), (V), (VI) or (VII) described hereinafter, J represents, —S—, —O—, the general formula

or the general formula

$R_7$ and $R_8$ are the same or different and represent hydrogen atom, alkyl or alkenyl, and $R_5$ and $R_6$ may form alkenylene

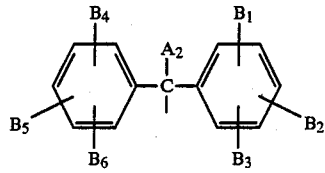

general formula (III)

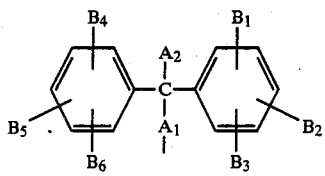

general formula (IV)

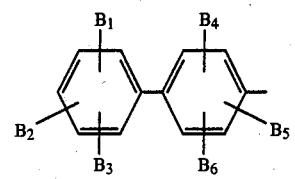

general formula (V)

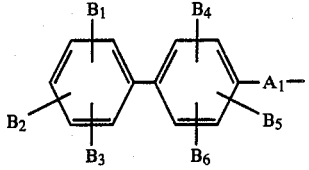

general formula (VI)

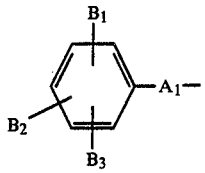

general formula (VII)

wherein $A_1$ represents alkylene, $A_2$ has the same meaning as that of $R_2$, $B_1$, $B_2$, $B_3$, $B_4$, $B_5$ or $B_6$ may be the same or different and represents hydrogen atom, alkyl, alkenyl, acyl, aryl, aralkyl, halogen atom, nitro, sulfo, carboxyl, hydroxyl, alkoxy or hydroxyalkyl.

8. A test composition according to claim 7 wherein said composition further contains a buffer reagent.

9. A test composition according to claim 7, wherein said composition further contains a member selected from the group consisting of a surfactant, antiseptics and ascorbate oxidase.

10. A test composition according to claim 7, wherein said composition further contains an enzymatic hydrogen peroxide-producing system.

11. A test composition according to claim 7, wherein said system contains oxidase.

* * * * *

UNITED STATES PATENT AND TRADEMARK OFFICE
CERTIFICATE OF CORRECTION

PATENT NO. : 4,916,058
DATED : April 10, 1990
INVENTOR(S) : Norihito Aoyama et al.

It is certified that error appears in the above-indentified patent and that said Letters Patent is hereby corrected as shown below:

Column 5

Table 2, Compound Nos. 31 to 34 should be deleted.

Signed and Sealed this

Sixteenth Day of July, 1996

Attest:

BRUCE LEHMAN

*Attesting Officer*      *Commissioner of Patents and Trademarks*